United States Patent [19]

Baijnath

[11] Patent Number: 4,887,616
[45] Date of Patent: Dec. 19, 1989

[54] RESTRAINT MITT FOR RESTRAINING A WEARER'S HAND AND ARM

[76] Inventor: Etienette Baijnath, No. 609 - 120 Raglan Avenue, Toronto, Ontario, M6C 2I4, Canada

[21] Appl. No.: 947,289

[22] Filed: Dec. 29, 1986

[30] Foreign Application Priority Data

Dec. 30, 1985 [CA] Canada .................................. 498,718

[51] Int. Cl.$^4$ ............................................. A61F 13/00
[52] U.S. Cl. .................................................. 128/879
[58] Field of Search ................... 128/133, 134, 132 R, 128/878, 879; 2/16, 18, 170

[56] References Cited

U.S. PATENT DOCUMENTS

| | | | |
|---|---|---|---|
| Re. 20,858 | 9/1938 | Moller | 128/879 |
| 1,298,158 | 3/1919 | Bartram | 128/879 |
| 1,537,811 | 5/1925 | Epling | 128/879 X |
| 2,493,977 | 1/1950 | Kochman | 2/18 |
| 2,706,477 | 4/1955 | Daake | 128/878 X |
| 3,176,683 | 4/1965 | Posey | 128/879 X |
| 3,185,476 | 5/1965 | Fechner | 2/18 X |
| 3,415,244 | 12/1968 | Block | 128/879 |
| 3,741,207 | 6/1973 | Fuson | 128/879 |
| 4,422,455 | 12/1983 | Olsen | 128/878 |
| 4,628,925 | 12/1986 | Witzel | 128/878 |

FOREIGN PATENT DOCUMENTS 0730310  8/1932  France ..................................... 2/170

Primary Examiner—Richard T. Stouffer

[57] ABSTRACT

Previously invented restraining mitts are known to fully or partially splint or immobilize the fingers. The mitt of the present invention has a cavity sufficiently large to permit the wearer's hand to be relatively freely movable therein to the extent of flexion and full extension of the fingers for optimum comfort, at all times. The cavity of the preferred mitt is defined by a sufficiently firm and, or thick shape retaining wall made of material such as firm, thick heat mouldable foam to prevent the wearer from grasping objects beyond the mitt. The top and bottom ends of the cavity are narrowed in relation to its middle portion. The given mitt may be worn by a child, confused, psychotic, or other appropriate patient or wearer for the prevention of the use of his/her hand, in cases where there is concern that an irresponsible patient as given above, may be endangered by removing, against medical advice, necessary treatment devices such as dressings, intravenous needles, input or output tubes etc. In addition, the mitt has a restraining strap that can be tied to a fixed structure to further protect the wearer and others, by preventing him/her from climbing out of bed or striking out at others.

1 Claim, 2 Drawing Sheets

RESTRAINT MITT FOR RESTRAINING A WEARER'S HAND AND ARM

BACKGROUND OF THE INVENTION

1. Field of the Invention

The present invention relates to a fingerless restraint mitt with means for restraining the hand and, or the arm.

2. Prior Art

Restraining mitts currently available, although functionally effective, generally fully or partially splint the outstretched hand or hold the hand in the formation of a fist. Under these conditions movements of the muscles and joints of the hand are unnaturally restricted to some degree. Such restricted movements may slow blood circulation and may also contribute to stiffness and discomfort of the hand. Restraint mitts generally available include: a restraining and exercising mitt with "rigidifying means," invented by John T. Posey, U.S. Pat. No. 3,176,683 dated Apr. 6, 1965; a flexible hand restraint mitt holding the hand in "fist formation," invented by A. G. Matukas, U.S. Pat. No. 3,476,108 dated Nov. 4, 1969 and a hand restraining mitt splinting the fingers in a natural curve, invented by Edith G. Fuson U.S. Pat. No. 3,741,207 dated June 26, 1973.

SUMMARY OF THE INVENTION

A restraining mitt that permits increased movements of the hand muscles and joints is needed in the area of patient care. I have found that this may be achieved by providing a mitt of which the wall is formed of sufficiently firm and, or thick shape retaining materials that define a sufficiently large cavity permitting full extension and flexion of the fingers.

BRIEF DESCRIPTION OF THE DRAWINGS

The embodiments of the invention are represented in the illustrative drawings below.

DESCRIPTION OF THE PREFERRED EMBODIMENT(S)

Several versions of the restraint mitt of the invention may be created of many physical embodiments depending on choice of materials, style and purpose for use. The preferred embodiments and the objects of one version of the invention are described and illustrated below, with the accompanying drawings enumerated above.

Figure 1:
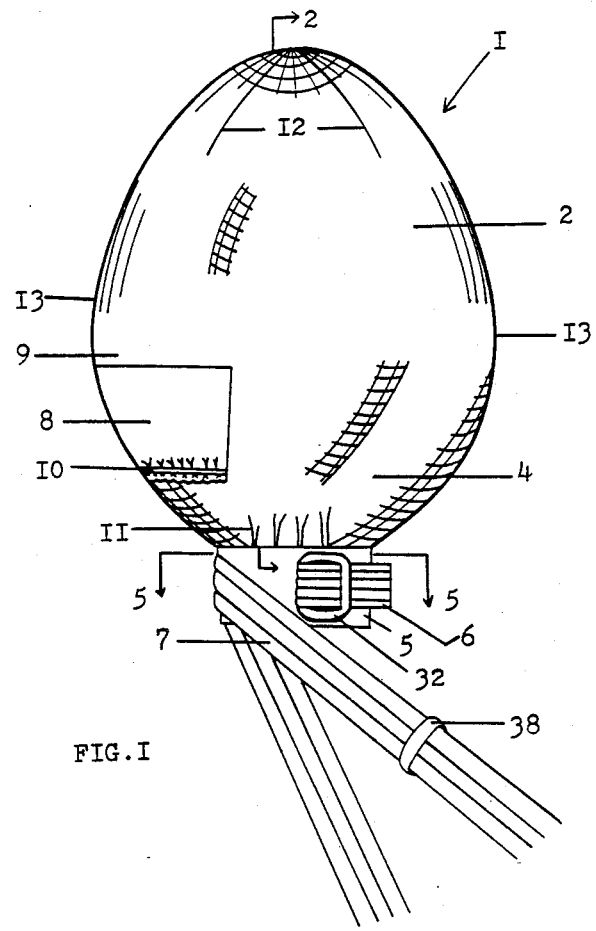
FIG. 1 is a perspective of one vertical palm-side view of one embodiment.

Referring first to FIG. 1, there is shown a restraint mitt 1 of the preferred embodiments of the present invention. The mitt includes a wall 2 comprised of firm heat mouldable foam that accommodates the wearer's hand. Connected to the wall of the mitt is a cuff 5 for retaining the wearer's hand within the body 2. Connected to the cuff is a 3 bar slide 32 and a durable security strap 6 for securing the mitt 1 to the wrist. In addition, a restraint strap 7 is connected to the cuff. The restraining strap is for restraining the wearer's arm to a bedstead: the left arm on the left side of the bed and the right arm on the right side of the bed. The strap is stored in a patch pocket 8, at times when the strap is not in use. The pocket is made of fabric and is stitched to the outer fabric covering 9 of the mitt 1. The top of the pocket is elasticized 10 serving to prevent the strap from falling out of the pocket after the strap is placed therein.

The fabric covering 9 is durable fabric and has curved darts 12 to shape the covering to fit the top end of the mitt. The covering is stitched along one or two side/s 13 to encircle the wall of the mitt horizontally, but leaving a short unstitched portion along one side, at the bottom end of the covering, for the opening/closure 22 of the mitt, shown in FIG. 4. In addition the lower border 11 of the covering is gathered to fit the bottom end of the wall 2.

Figure 2:
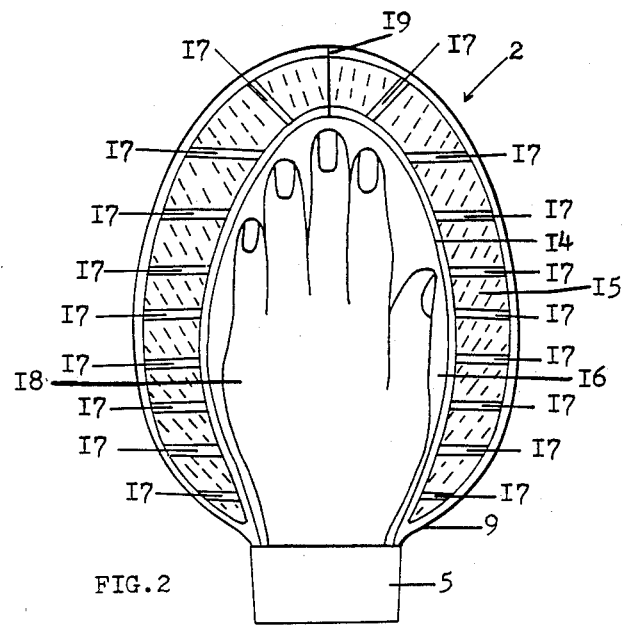
FIG. 2 is a sectional, partly perspective view through a vertical mid-line of line 2—2 of FIG. 1, showing one structure of the wall of the preferred mitt and one form of its cavity.

As shown in FIG. 2, a vertical section of line 2—2 the preferred structure of the mitt 1 comprises the absorbent lining 14, the foam wall 15 and the outer covering 9. The lining is absorbent cotton, flannelette or other fabric and lies around the wearer's hand, next to the skin for the purposes of protecting the skin and absorbing perspiration. The lining 14 is shaped and sewn in a similar way to the outer covering 9, but is scaled down to size to fit the cavity 16. A portion of one side of the lining is left unstitched to match the unstitched portion of the adjacent side of the covering of the mitt.

The wall 15 of the mitt 1, made of sufficiently firm, thick heat mouldable foam, defines the shape of the cavity 16, wherein the top and bottom ends of the given cavity are narrowed in relation to the cavity's middle portion, and is sufficiently firm and, or thick to maintain the shape of the cavity and prevent the wearer from grasping objects external to the mitt. Thus the mitt functions effectively in cases where medical and legal factors necessitate its use. The components of the mitt may be selected for making the mitt a disposable or reusable one. The moulded foam wall 15 has numerous air holes 17 for ventillating the cavity. The air holes communicate with the cavity and room air and are spaced at horizontal and vertical intervals over the entire wall, with increasing frequency, in the area of the palm of the hand 18. The cavity is ventillated in order to reduce heat and perspiration build up after the wearer's hand is inserted into the cavity.

Figure 3:
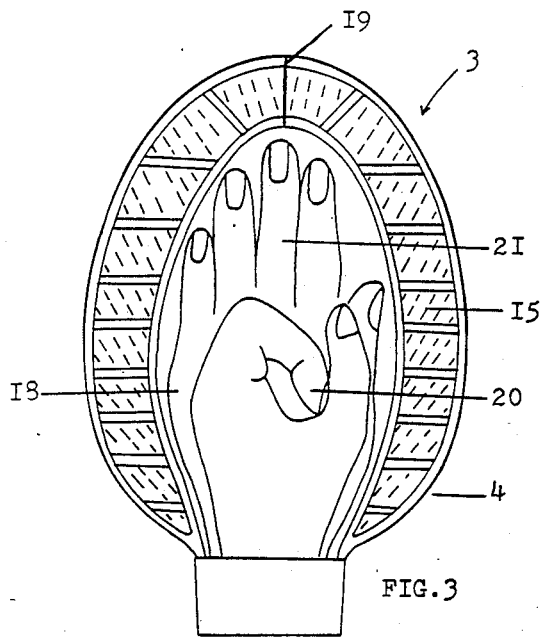
FIG. 3 is a replica of FIG. 2 except FIG. 3 further shows flexion and full extension of the fingers within one form of the embodiment in FIG. 1.

The embodiments of FIG. 3 are identical with FIG. 2, except FIG. 3 further shows flexion 20 and full extension 21 of the fingers within the cavity 16. The cavity is sufficiently long, wide and deep permitting the wearer's hand to be freely movable therein to the extent of full extension and flexion of the fingers. Thus the wearer may move his fingers and exercise the muscles and joints of his hand, thus maintaining his/her level of blood circulation and function of his/her hand and consequently minimizing fatigue, stiffness and discomfort of the hand, across time.

Figure 4:
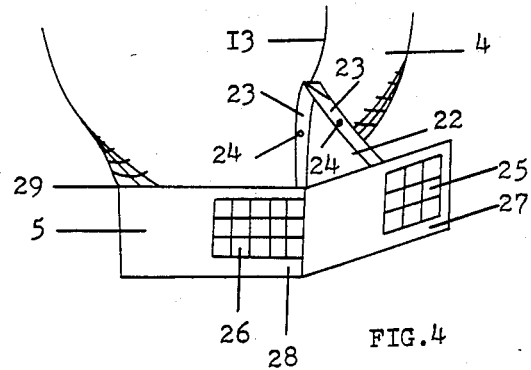
FIG. 4 is a perspective view of the bottom end of the embodiment of FIG. 1, showing one version of a side opening/closure, in the given area, and extending through a cuff.

As shown in FIG. 4 the bottom part of the preferred mitt 1 is rotated to illustrate the side seam 13 and the opening 22, situated on the ulnar side of the forearm. The opening permits easy insertion of the wearer's hand into the mitt. To create this opening, the foam structure has a short vertical slit in the bottom end that is aligned with the unstitched portions of the inner lining 14 and the outer covering 9. The unstitched portions of the lining and covering are stitched separately immediately off the periphery of the foam slit forming a placket 23 that extends to the top of the cuff 5, thus forming the closure or opening 22. The placket may be held in a closed position by the snap 24. VELCRO hook and loop fastening tapes 25 and 26 are stitched to the open ends 27 and 28 of the cuff 5. The overlapping end 27 of the cuff has a short Velcro hook tape 25 whereas the other end 28 has a long Velcro loop tape 26. In the closed position the short tape lies over the long tape. The long and short Velcro hook and loop tapes have been used to make for adjustable sizing of the cuff to fit the wearer's wrist snugly in cases where the wrist is slightly smaller or larger than the average wrist size, of a given size mitt.

Figure 5:
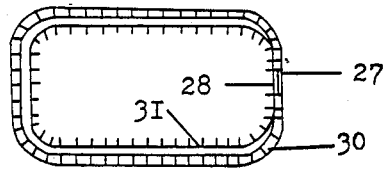
FIG. 5 is a sectional view of line 5—5 in FIG. 1 showing components of one type of cuff.

The basic construction of the cuff 5 as shown in FIG. 5 comprises an outer layer of durable fabric 30 and a soft plush or fleecy fabric 31 to minimize compression of the wrist from the securing means of the mitt.

To connect the cuff to the mitt, the top border of the outer layer of the cuff 5 is stitched together with the bottom borders of covering 9 and lining 14 of the body 2 (shown in FIG. 2,) immediately outside the periphery of the bottom end of the foam wall of the mitt, along line 29, from the outer side of the placket 23 to the other outer side of the placket 23; so that the entire foam wall 15 (FIG. 2) is enveloped in the outer covering and lining of the mitt. The wrist is, therefore, permitted flexion and extension during use of the mitt. The outer layer 30 of the cuff is subsequently stitched to the fleecy underlayer 31, along all the borders of cuff 5.

Figure 6:
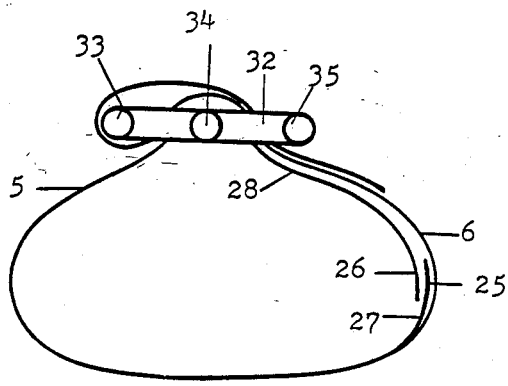
FIG. 6 is a diagrammatic illustration of a bottom view of one version of means for securing the cuff of the embodiment in FIG. 1.

In FIGS. 6 the means for securing the mitt to the wearer's wrist is diagrammatically shown to be connected to the cuff and comprises a durable security strap 6 and a "3 bar slide" 32. The security strap is stitched to the outside of the overlapping end 27 of the cuff, while the bar slide is tacked on the outside of the other end 28 and is situated on the under surface of the forearm, beyond the long Velcro loop tape 26 on the underside of the forearm. When the security strap is engaged in the bar slide, said strap secures the opening of the mitt in a closed position. The security strap 6 is threaded through the bar slide in the usual way, whereby the strap enters the bar slide by passing under the right bar 35, over the center bar 34 and under and out of the left bar 33. For the purpose of this invention additional threading is necessary to prevent security strap 6 from sliding loose in the bar slide. The security strap is consequently, further reflected over the left bar 33, over the center bar, passing under and out the right bar.

Figure 7:
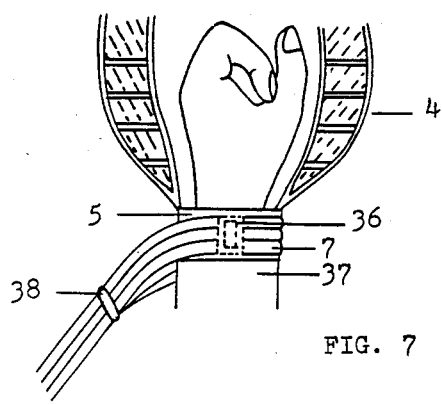
FIG. 7 is a view of the bottom half of FIG. 3, except FIG. 7 further shows a perspective view of one form of restraining means connected to the cuff.

As shown in FIG. 7 a durable restraint strap 7 is well stitched 36 for strength to the cuff 5 on the anterior radial side of the forearm 37. The restraint strap is sufficiently long to be tied to the bedstead. The strap is worn around the cuffed forearm and is loosely held together by loop 38 to reduce stress on the stitching 36 when pressure is applied to the restraint strap 7, should the wearer tug on the strap after it is tied to the bedstead. To prevent loss of the strap, said strap is permanently stitched to the cuff.

In order to make it very difficult for the wearer to undo the security strap 6, the restraint strap 7 running along the under side of the forearm may be taped flush to the end of the security strap with adhesive tape, immediately beyond the threaded bar slide.

I claim:

1. A restraint mitt for restraining a wearer's hand and arm comprising:
   (a) a fingerless mitt comprised of a wall sufficiently firm to maintain its shape and to prevent the wearer from grasping objects external to the mitt, said wall enclosing a concave cavity, the top and bottom ends of said cavity being narrowed in relation to the cavity's middle portion, said cavity being adapted to contain a wearer's hand while permitting the wearer's hand to be relatively freely movable therein;
   (b) a durable protective cover covering the outside of the wall of the mitt and a durable absorbent lining, lining the cavity of said wall;
   (c) retaining means at the bottom end of the mitt comprised of a durable cuff open on one side and having a compression-reducing under layer to reduce compression on the wearer's wrist;
   (d) noninjurious securing means on said cuff comprising hook and loop fastening means for closing the open side of the cuff, a buckle and a security strap fixed to the cuff, wherein the security strap is adapted to be threaded through the buckle in such a manner that the security strap will not slip out of the buckle;
   (e) restraining means comprised of a restraining strap having an intermediate point fixed to the cuff, said restraining strap having a tab loop holding the restraining strap together near the cuff, wherein part of the restraining strap passes through the tab loop securing the restraining strap around the cuff and two free parts of the restraining strap beyond the tab loop are adapted to be secured to a fixed structure;
   (f) and means for storing the two free parts of the restraining strap, when they are not attached to a fixed structure, comprising a patch pocket secured to the cover of the mitt, said pocket having an elasticised mouth for retaining the free parts of the restraining strap therein.

* * * * *